United States Patent [19]

Sayer et al.

[11] Patent Number: 5,324,745
[45] Date of Patent: Jun. 28, 1994

[54] SOLID PESTICIDAL FORMULATION, A PROCESS FOR ITS PREPARATION AND THE USE THEREOF

[75] Inventors: Michael G. Sayer, Gillingham, England; Alister C. Hill, Sittingbourne, Great Britain; Teresa J. Reid, Sittingbourne, Great Britain; Brian D. Steer, Sittingbourne, Great Britain

[73] Assignee: Shell Research Limited, United Kingdom

[21] Appl. No.: 562,927

[22] Filed: Aug. 6, 1990

[30] Foreign Application Priority Data

Aug. 17, 1989 [GB] United Kingdom ............... 8918807

[51] Int. Cl.$^5$ .............................................. A01N 55/04
[52] U.S. Cl. ................................................... 514/493
[58] Field of Search ............................................ 514/493

[56] References Cited

U.S. PATENT DOCUMENTS

| | | | |
|---|---|---|---|
| 3,264,177 | 8/1966 | Kenaga | 167/30 |
| 3,268,395 | 8/1966 | Taylor | 167/30 |
| 3,321,361 | 5/1967 | Menn et al. | 167/22 |
| 3,389,048 | 6/1968 | Kenaga | 167/46 |
| 3,445,575 | 5/1969 | Taylor | 424/288 |
| 3,499,086 | 3/1970 | Bruneckner et al. | 424/286 |
| 3,907,818 | 9/1975 | Buchel et al. | 260/299 |
| 3,988,449 | 10/1976 | Buchel et al. | 424/245 |
| 4,010,276 | 3/1977 | Gitlitz | 424/288 |
| 4,791,139 | 12/1988 | Bushnell et al. | 514/721 |
| 4,871,757 | 10/1989 | Lüthy et al. | 514/383 |

FOREIGN PATENT DOCUMENTS

| | | |
|---|---|---|
| 0057035 | 8/1982 | European Pat. Off. . |
| 0127773 | 12/1984 | European Pat. Off. . |
| 1327336 | 8/1973 | United Kingdom . |
| 1369148 | 10/1974 | United Kingdom . |

OTHER PUBLICATIONS

Merck Index 10th ed #7594 1983.

*Primary Examiner*—Frederick E. Waddell
*Assistant Examiner*—Russell Travers

[57] ABSTRACT

A pesticidal organotin formulation is a water dispersible solid concentrate comprising at least one pesticidal organotin compound and polyvinylpyrrolidone. The formulation is prepared by dissolving the organotin compound and the polyvinylpyrrolidone in a solvent, followed by removal of the solvent, preferably by evaporation at a pressure below atmospheric pressure to yield the solid concentrate. The formulation may be dispersed in water, either with or without agitation, to yield an aqueous dispersion which may be applied to a locus to combat pests, especially acarids.

5 Claims, No Drawings

SOLID PESTICIDAL FORMULATION, A PROCESS FOR ITS PREPARATION AND THE USE THEREOF

The present invention relates to a solid pesticidal formulation having as active ingredient an organotin compound, to a process for preparing such a a formulation, and to the use of such a formulation in combating pests.

It is known from UK Patent Nos. 1,327,336 and 1,369,148, from U.S. Pat. Nos. 3,264,177, 3,389,048 and 3,499,086, and from German Patent No. 2,143,252, that various organotin compounds are active as pesticides. In particular, U.S. Pat. Nos. 3,264,177 and 3,389,048 and German Patent No. 2,143, 252 disclose that certain tricyclohexyl tin derivatives are active as acaricides. Further, from UK Patent No. 1,327,336 it is known that certain trineophyl tin derivatives are active against acarids.

A number of formulations have been proposed for organotin pesticides. Details of commercially available organotin pesticidal formulations are given in "The Pesticide Manual", 8th Edition, British Crop Protection Council. Commercial examples of tricyclohexyl tin derivatives that have been available include azocyclotin, sold as a wettable powder formulation under the trade mark "PEROPAL" by Bayer, and cyhexatin, sold both as a wettable powder formulation under the trade mark "PLICTRAN" and as a suspension concentrate formulation under the trade mark "DORVERT" by Dow Chemical Company. Commercial examples of trineophyl tin derivatives include fenbutatin oxide, sold both as a wettable powder formulation and a suspension concentrate formulation under the trade mark "TORQUE" by "Shell".

In European Patent Specification 0 057 035 B (EP-B-0,057,035) an emulsifiable concentrate formulation of a tricyclohexyl tin or trineophyl tin derivative has been proposed, together with a process for its preparation. The formulation disclosed is a water dispersible liquid formulation comprising at least one emulsifier, at least one saturated or unsaturated mono- or di- hydric alcohol optionally substituted by one or more alkoxy, alkoxyalkoxy, alkoxycarbonyl, alkylcarbonyl, alkylcarbonyloxy or aryl groups and dissolved therein a tricyclohexyl tin or trineophyl tin oxide or hydroxide. In the specification of EP-B-0,057,035 it is stated that emulsifiable concentrates generally have advantages over wettable powders and suspension concentrates; for example they may be more simply prepared using technically less sophisticated facilities and they allow more ready attainment of fine dispersions in water for application to a treatment site. However, a disadvantage of emulsifiable concentrates lies in the presence of organic solvents, such as hydrocarbons, in the formulation which, after dispersion of the concentrate in water, are applied to the treatment site along with the active ingredient. The presence of solvents in the concentrate formulation and the use of solvents in this way may be environmentally undesirable.

The specification of European Patent Application Publication No. 0 127 773 (EP-A-0,127,773) discloses a solid pesticidal composition comprising a pesticide, an emulsifier or dispersing agent for the pesticide, and a self-disintegrating agent capable of effervescing or swelling on being contacted with water. The pesticide is disclosed as conveniently comprising a synthetic pyrethroid. Synthetic pyrethroids named in EP-A-0,127,773 are those known as permethrin (3-phenoxybenzyl-($\pm$)-cis, trans-2,2-dimethyl-3-(2,2- dichlorovinyl) cyclopropane-1-carboxylate), deltamethrin (S--cyano-3-phenoxy-benzyl-(IR,3R) 2,2-dimethyl-3- (2,2-dibromo vinyl)cyclopropane-1-carboxylate) and tetramethrin (3,4,5,6-tetrahydrophthalimidomethyl ($\pm$)cis, trans-chrysanthemate). Other named pesticides which can be used are propoxur (2-isopropoxyphenyl methyl-carbamate), trichlorfon (2,2-trichloro-1-hydroxy-ethylphosphonate), dichlorvos (2,2-dichlorovinyl demethyl phosphate), fenvalerate ( -cyano-3-phenoxy benzyl-(RS)-2(4-chlorophenyl)-3-methylbutyrate), diazinon (0,0-diethyl-0-2-isopropyl-6-methyl-pyrimidin-4-ylphosphorothioate), amitraz (N,N di-(2,4-xylylimino-methyl)methyl amine), phosmet (0,0-dimethyl S-phthalimido-methyl phosphorodithioate) and dursban (0,0-diethyl-0-3,5,6- trichloro-2-pyridyl-phosphorothioate).

Examples of self-disintegrating agents that can be used are a cross-linked polyvinylpyrrolidone or an acid/base combination, such as tartaric acid and an alkali metal carbonate or bicarbonate, particularly sodium bicarbonate. The specification of EP-A-0,127,773 is particularly directed to a composition in the form of a tablet.

A solid pesticidal composition of the kind disclosed in EP-A-0,127,773 offers the advantage over emulsifiable concentrates that the need for the presence of organic solvents in either the concentrate or the dispersion is removed. However, it has been found that solid composition of the kind disclosed in EP-A-0,127,773 having as active ingredient a pyrethroid insecticide of the type listed in EP-A-0,127,773 exhibit a biological activity no greater than the comparable suspension concentrate formulations.

It has now been found that organotin pesticides may be formulated into a solid concentrate which possesses the aforementioned advantages associated with an emulsifiable concentrate, namely a technically simple preparation of the formulation and a ready and rapid dispersion in water, but which obviates the need for the presence of organic solvents in either the concentrate formulation or the aqueous dispersions.

Most surprisingly, however, a solid concentrate pesticidal organotin formulation has been found which exhibits a significantly increased biological activity compared to that of the corresponding commercially available suspension concentrate.

Accordingly, the present invention provides a pesticidal organotin formulation, characterised in that it is a water dispersible solid concentrate comprising polyvinylpyrrolidone and at least one pesticidal organotin compound.

The minimum quantity of organotin compound present in the formulation of the present invention is determined by the concentration of organotin compound required in an aqueous dispersion of the formulation to achieve the desired effect of applying the dispersion to a treatment site. The maximum quantity of organotin compound in the formulation is dependent upon the desired extent and rate of dispersion of the formulation in water and may be readily determined by routine experimentation. The quantity of organotin compound present in the formulation is preferably in the range of from 5% w/w to 60% w/w, more preferably in the range of from 10% w/w to 50% w/w, most preferably in the range of from 30 % w/w to 40% w/w. The formulation may comprise one or more active ingredients selected from any of the pesticidally active organotin compounds. However, the preferred organotin compounds are tricyclohexyl tin derivatives and trineophyl tin derivatives. The most preferred compounds are trineophyl tin derivatives. Incorporation of fenbutatin oxide (bis[tris(2-methyl-2-phenylpropyl)-tin]oxide) in the formulation is especially preferred.

Throughout this specification and claims, the term "neophyl" is used to indicate "2-methyl-2-phenylpropyl".

The minimum quantity of polyvinylpyrrolidone in the formulation of the present invention is dependent upon the desired extent and rate of dispersion of the formulation in water. The quantity of polyvinylpyrrolidone present in the formulation is preferably greater than 50% w/w, more preferably in the range of from 50% w/w to 90% w/w, the most preferred range being from 60% w/w to 70% w/w. Preferably, the polyvinylpyrrolidone has an average molecular weight in the range of from 10,000 to 400,000. Commercially available polyvinylpyrrolidone suitable for inclusion in the formulation of the present invention, includes the range of solid PVP K products sold by the GAF Corporation. A most suitable product in this range is PVP K-30 having an average molecular weight of about 40,000.

In addition to an organotin pesticide and polyvinylpyrrolidone, the formulation of the present invention may comprise other components common to the art of pesticidal formulations, for example surface active agents, corrosion inhibitors and stabilizers. In addition, the formulation may comprise one or more inert fillers. However, if the aforementioned other components or fillers are present in the formulation, the ratio of organotin compound to polyvinylpyrrolidone is preferably in the range of from 1:1 to 1:5, most preferably from about 1:2 to 1:3.

Inclusion of a surface active agent in the formulation is not necessary to ensure a ready and rapid dispersion of the organotin compound in water. However, examples of suitable surface active agents that may be included in the formulation are the sodium or calcium salts of polyacrylic acids and lignin sulphonic acids and sodium or calcium salts of carboxylic acids. A group of the most suitable surface active agent are the sodium lignosulfonates, for example the commercial product "VANISPERSE" (Trade Mark).

Suitable inert fillers for inclusion in the formulation include natural and synthetic clays and silicates, for example natural silicas such as diatomaceous earths; magnesium silicates, for example talcs; magnesium aluminium silicates, for example kaolinites, montmorillonites and micas; calcium carbonate, calcium sulphate; ammonium sulphate; synthetic calcium or aluminium silicates; elements, for example carbon and sulphur; natural and synthetic resins, for example coumarone resins, polyvinyl chloride, and styrene polymers and copolymers; solid polychlorophenols and solid fertilisers, for example superphosphates.

According to a further aspect of the present invention there is provided a process for the preparation of a formulation as hereinbefore described, which comprises dissolving polyvinylpyrrolidone and at least one pesticidal organotin compound in a solvent, followed by removal of the solvent from the resulting solution to yield the solid concentrate.

The solvent selected for use in the process for the preparation of the formulation must be one in which both the organotin compound and polyvinylpyrrolidone are sufficiently soluble to form the desired formulation. Such solvents are readily identifiable by routine experimentation. Examples of suitable solvents include haloalkanes, preferably having from one to eight carbon atoms, more preferably from one to four carbon atoms, and alcohols, preferably the lower alcohols having from one to eight carbon atoms, more preferably one to four carbon atoms. Preferred solvents are chloroalkanes having from one to four carbon atoms, with dichloromethane and trichloromethane being especially preferred.

Removal of the solvent may be effected by methods well known to a person skilled in the art, for example by allowing the solution of the organotin compound and polyvinylpyrrolidone to stand and allowing the solvent to evaporate. Preferably, the solvent is removed from the solution by evaporation at a pressure below atmospheric pressure. Evaporation of the solvent at a pressure below atmospheric pressure may be effected using conventional vacuum drying techniques and apparatus at a pressure down to the minimum operating pressure of the apparatus. Solvent removal is preferably effected at a pressure below 400 mbar. Alternatively, solvent removal may be effected by conventional spray drying techniques. As a further alternative, the solvent may be removed by treating the solution with a further solvent to cause the organotin compound and polyvinylpyrrolidone to precipitate. Such further solvents are readily identified by routine experiment. One example of such a solvent is hexane.

If the formulation is to comprise any other components common to the art, as mentioned above, these may conveniently be dissolved in or suspended in the solution of the organotin compound and polyvinylpyrrolidone prior to solvent removal.

Once the solvent has been removed, the resulting solid concentrate may be crushed or ground to reduce the particle size and so aid dispersion. If the formulation is to comprise one or more inert fillers, these may conveniently be added to the solid concentrate at this stage.

According to a further aspect of the present invention there is provided an aqueous dispersion of a pesticidal organotin compound, prepared by dispersing in water a formulation as hereinbefore described. Dispersion of the formulation may be effected using standard techniques existing in the art. However, it is a further surprising feature of the formulation of the present invention that the highest rate of dispersion of the organotin compound is achieved without agitation of the water. The formulation may simply be placed on the surface of the water from where the organotin compound rapidly disperses throughout the volume of the water. Agitation of the water may be necessary once the formulation has dispersed to achieve a homogeneous aqueous dispersion, particularly when preparing the aqueous dispersion in large volumes.

As an alternative method of dispersion, the formulation may be packed in bags formed from a water soluble polymer, for example polyvinylacetate. Addition of such bags to the water causes the water soluble polymer to dissolve, releasing the contents to disperse as before.

Further, in accordance with another aspect of the present invention, there is provided a method of combating pests at a locus, which comprises applying to the locus an aqueous dispersion of the formulation as hereinbefore described.

The present invention is illustrated by the following Examples.

EXAMPLE 1

A solid concentrate formulation was prepared from the following components:

| technical fenbutatin oxide | 300 g |
|---|---|
| K-30 (polyvinylpyrrolidone average molecular weight 40,000) | 700 g |
| dichloromethane | 1500 ml |

The fenbutatin oxide and the polyvinylpyrrolidone were added gradually to the dichloromethane whilst stirring until dissolution was complete. The dichloromethane was evaporated from the resulting solution using conventional vacuum drying apparatus at a pressure of 200 m bar, to yield the desired formulation in the form of a white solid. The white solid was lightly ground. The resulting formulation dispersed readily upon addition to water without stirring to give a homogeneous aqueous dispersion.

EXAMPLE 2

A solid concentrate formulation was prepared from the following components:

| technical fenbutatin oxide | 300 g |
|---|---|
| K-30 (polyvinylpyrrolidone average molecular weight 40,000) | 650 g |
| VANISPERSE (TRADE MARK) (surface active agent) | 50 g |
| dichloromethane | 1500 ml |

The fenbutatin oxide and the polyvinylpyrrolidione were added gradually to the dichloromethane whilst stirring until dissolution was complete. The surface active agent was added gradually to the resulting solution whilst stirring until a fine supension of the surface active agent in the solution had been achieved. The resulting mixture was placed in conventional vacuum drying apparatus and the dichloromethane evaporated at a pressure of 200 m bar, to yield the desired formulation in the form of a brown solid. The brown solid was lightly ground. The resulting formulation dispersed readily upon addition to water without stirring to yield a homogeneous aqueous dispersion.

EXAMPLE 3

A solid concentrate formulation was prepared from the following components:

| technical fenbutatin oxide | 300 g |
|---|---|
| K-30 (polyvinylpyrrolidone average molecular weight 40,000) | 700 g |
| isobutanol | 1500 ml |

The general procedure of Example 1 was followed to yield the desired formulation in the form of a white solid, which was lightly ground. Upon addition to water, the resulting formulation readily dispersed without agitation to form a homogeneous aqueous dispersion.

EXAMPLE 4

A solid concentrate formulation was prepared from the following components:

| technical fenbutatin oxide | 300 g |
|---|---|
| K-30 (polyvinylpyrrolidone average molecular weight 40,000) | 700 g |
| octanol | 1500 ml |

The general procedure of Example 1 was followed to yield the desired formulation in the form of a white solid, which was lightly ground. Upon addition to water, the resulting formulation readily dispersed without agitation to form a homogeneous aqueous dispersion.

EXAMPLE 5

Dispersion of formulation i) An aqueous dispersion was formed from the formulation of Example 1 (0.04 g) and water (100 ml), having a concentration of 12g of active ingredient/100 liters. The formulation, was scattered on the surface of the water and allowed to stand without agitation. The formulation fully dispersed in under 5 minutes to yield an aqueous dispersion having an initial particle size of 500 nm. The resulting dispersion was allowed to stand for 3 hours, after which time the particle size was again measured, revealing that particle growth had not occurred and that the particle size remained 500 nm.

ii) An aqueous dispersion was formed from the formulation of Example 2 (0.04 g) and water (100 ml), having a concentration of 12 g of active ingredient/100 liters. The formulation was scattered on the surface of the water and the resulting mixture allowed to stand without agitation. The formulation fully dispersed in under 5 minutes to yield an aqueous dispersion having an initial particle size of 500 nm. The dispersion was allowed to stand for 3 hours, after which time the particle size had increased to 1.5 $\mu$m.

iii) An aqueous dispersion was formed from the formulation of Example 1 (0.04 g) and water (100 ml), having a concentration of 12 g of active ingredient/100 liters. The formulation was scattered on the surface of the water and the water stirred. The formulation dispersed in 8 minutes to yield an aqueous dispersion having an initial particle size of 200 nm.

Biological Activity

The acaricidal activity of the formulation of the present invention was determined in a number of tests. The details and the results of the tests are set out in Examples 6 to 11 below.

EXAMPLE 6

A solid concentrate formulation of polyvinylpyrrolidone and fenbutatin oxide (333 g/kg) was prepared using the general method of Example 1. The acaricidal activity of this formulation was compared with that of the standard commercially available suspension concentrate formulation of fenbutatin oxide containing 550 g/l active ingredient (sold under the trade mark "TORQUE") and the commercial acaricide "MEOTHRIN" (trade mark), an emulsifiable concentrate containing 100 g/l of the pyrethroid fenpropathrin (cyano(3-phenoxyphenyl)-methyl 2,2,3,3-tetramethylcyclopropanecarboxylate). Each of the formulations of fenbutatin oxide was dispersed in water to form three dispersions having a range of concentrations of active ingredient (40 ppm, 20 ppm and 10 ppm). Aqueous dispersions of the fenpropathrin formulation were prepared having concentrations of active ingredient of 40 ppm and 20 ppm.

Each dispersion was applied to three french bean plants (*Phaseolus vulgaris* cv. The Prince) using a hand held gravity fed mist gun at a rate of 1000 l/ha. The spray deposits were allowed to dry, after which each plant was infested with from 200 to 300 laboratory reared adult and immature stages of the two-spotted spider mite, *Tetranychus urticae*. After 3 weeks, the mite population on the new growth of plant since spraying was assessed by estimating the percentage of leaf area damaged by feeding mites, with 0% representing no damage and 100% representing plant death with a total bleaching of the foliage.

The results, in the form of an average leaf damage for the three plants treated, of two separate tests are set out in Table 1 below.

TABLE 1

|  | active ingredient (ppm) | Leaf damage (%) Test 1 | Leaf damage (%) Test 2 |
| --- | --- | --- | --- |
| solid concentrate fenbutatin oxide (333 g/kg) and polyvinylpyrrolidone | 40 | 2.5 | 2.8 |
|  | 20 | 10.2 | 8.3 |
|  | 10 | 13.6 | 45.5 |
| standard suspension concentrate fenbutatin oxide (550 g/l) | 40 | 15.8 | 48.9 |
|  | 20 | 18.5 | 52.5 |
|  | 10 | 73.1 | 59.8 |
| standard emulsifiable concentrate fenpropathrin (100 g/l) | 40 | not tested | 36.6 |
|  | 20 | 52.3 | not tested |

EXAMPLE 7

A solid concentrate formulation of polyvinylpyrrolidone, fenbutatin oxide (350 g/kg) and the surface active agent VANISPERSE (trade mark) (100 g/kg) was prepared using the general method of Example 2. The general test procedure described in Example 6 was followed, the results of which are set out in Table 2 below.

TABLE 2

|  | active ingredient (ppm) | Leaf damage (%) |
| --- | --- | --- |
| solid concentrate fenbutatin oxide (350 g/kg) VANISPERSE (trade mark) (100 g/kg) polyvinylpyrrolidone | 40 | 3.3 |
|  | 20 | 2.6 |
|  | 10 | 27.6 |
| standard suspension concentrate fenbutatin oxide (550 g/l) | 40 | 9.2 |
|  | 20 | 33.0 |
|  | 10 | 73.5 |
| standard emulsifiable concentrate fenpropathrin (100 g/l) | 40 | 85.9 |

The results set out in Tables 1 and 2 clearly demonstrate that the solid concentrate organotin formulation of the present invention exhibits significantly superior acaricidal activity compared with the corresponding commercially available suspension concentrate and a standard pyrethroid emulsifiable concentrate formulation.

EXAMPLE 8

The acaricidal activity of the solid concentrate formulation and the standard suspension concentrate formulation of fenbutatin oxide described in Example 1 were subjected to further tests.

Each of the fenbutatin oxide formulations was dispersed in water to form a range of aqueous dispersions having concentrations in the range of from 0.00094% w/w to 0.015% w/w active ingredient. Each aqueous dispersion was applied to leaf discs cut from French bean plants at a volume rate of 380 l/ha using a standard spray apparatus. The spray deposits were allowed to dry, after which each leaf disc was infested with ten adult female two-spotted spider mites, *Tetranychus urticae*. The number of moribund and dead mites was recorded after 48, 72 and 96 hours.

Two such tests were conducted. For each test an $LC_{50}$ (the dosage of active ingredient required to kill half of the test species) for each formulation was calculated from the mortality figures. A toxicity index for the solid concentrate formulation was calculated thus:

$$\text{toxicity index} = \frac{LC_{50} \text{ suspension concentrate}}{LC_{50} \text{ solid concentrate}} \times 100$$

The results of the two tests are set out in Table 3 below.

TABLE 3

|  |  | Test 1 | Test 1 | Test 2 | Test 2 |
| --- | --- | --- | --- | --- | --- |
|  | Time (hr) | $LC_{50}$ (%) | Toxicity Index | $LC_{50}$ (%) | Toxicity Index |
| solid concentrate fenbutatin oxide (333 g/kg) and polyvinylpyrrolidone | 48 | 0.006 | >250 | 0.0076 | >200 |
|  | 72 | 0.0031 | 450 | 0.0041 | 330 |
|  | 96 | 0.0016 | 390 | 0.002 | 350 |
| standard suspension concentrate fenbutatin oxide (550 g/l) | 48 | >0.015 | — | >0.015 | — |
|  | 72 | 0.014 | 100 | 0.013 | 100 |
|  | 96 | 0.0061 | 100 | 0.0071 | 100 |

EXAMPLE 9

A solid concentrate formulation of polyvinylpyrrolidene, fenbutatin oxide (350 g/kg) and the surface active agent VANISPERSE (trade mark) (100 g/kg) was prepared using the general method of Example 2. The general test procedure described in Example 8 was followed, the results of which are set out in Table 4 below.

TABLE 4

|  |  | Test 1 | Test 1 | Test 2 | Test 2 |
| --- | --- | --- | --- | --- | --- |
|  | Time (hr) | $LC_{50}$ (%) | Toxicity Index | $LC_{50}$ (%) | Toxicity Index |
| solid concentrate fenbutatin oxide (350 g/kg) VANISPERSE (trade mark) (100 g/kg) polyvinylpyrrolidone | 48 | 0.0065 | >230 | 0.0072 | >210 |
|  | 72 | 0.0029 | 520 | 0.0030 | 370 |
|  | 96 | 0.0017 | 290 | 0.0021 | 200 |
| standard suspension concentrate fenbutatin oxide | 48 | >0.015 | — | >0.015 | — |
|  | 72 | 0.015 | 100 | 0.011 | 100 |
|  | 96 | 0.0049 | 100 | 0.0042 | 100 |

TABLE 4-continued

| | Test 1 | | Test 2 | |
|---|---|---|---|---|
| Time (hr) | $LC_{50}$ (%) | Toxicity Index | $LC_{50}$ (%) | Toxicity Index |
| (550 g/l) | | | | |

The results set out in Tables 3 and 4 demonstrate that the solid concentrate organotin formulation of the present invention exhibits both a greater speed of action and a superior acaricidal activity compared with the corresponding commercial suspension concentrate. After 72 hours, the solid concentrate formulation exhibited between 3 and 6 times the level of acaricidal activity of the suspension concentrate.

EXAMPLE 10

The acaricidal activity of the solid concentrate formulation and the standard suspension concentrate formulation of fenbutatin oxide described in Example 1 were subjected to further tests.

Each of the fenbutatin oxide formulations was dispersed in water to form a range of aqueous dispersions having concentrations in the range of from 0.00094% w/w to 0.015% w/w active ingredient. Each aqueous dispersion was applied to leaf discs cut from French bean plants at a volume rate of 380 l/ha using a standard spray apparatus. The spray deposits were allowed to dry, after which each leaf disc was infested with ten adult female two-spotted spider mites, *Tetranychus urticae*. After a period of 5 days the number of eggs laid by the female mites was counted and compared with the number of eggs laid by an equal number of female mites placed on untreated leaf discs at the beginning of the test.

Two such tests were conducted. For each test an $EC_{50}$ (the dosage of active ingredient required to reduce by 50% the number of eggs laid over the 5 day test period) for each formulation was calculated from the results. A toxicity index (egg) for the solid concentrate formulation was calculated thus:

$$\text{toxicity index (egg)} = \frac{EC_{50} \text{ suspension concentrate}}{EC_{50} \text{ solid concentrate}} \times 100$$

The results of the two tests are set out in Table 5 below.

TABLE 5

| | Test 1 | | Test 2 | |
|---|---|---|---|---|
| | $EC_{50}$ (%) | Toxicity Index (egg) | $EC_{50}$ (%) | Toxicity Index (egg) |
| solid concentrate fenbutatin oxide (333 g/kg) VANISPERSE (trade mark) (100 g/kg) polyvinyl-pyrrolidone | 0.0035 | 340 | 0.0027 | 840 |
| standard suspension concentrate fenbutatin oxide (550 g/l) | 0.012 | 100 | 0.022 | 100 |

EXAMPLE 11

The solid concentrate formulation of polyvinylpyrrolidone, fenbutatin oxide (350 g/kg) and the surface active agent VANISPERSE (trade mark) (100 g/kg) was prepared using the general method of Example 2. The general test procedure of Example 10 was followed, the results of which are set out in Table 6 below.

TABLE 6

| | Test 1 | | Test 2 | |
|---|---|---|---|---|
| | $EC_{50}$ (%) | Toxicity Index (egg) | $EC_{50}$ (%) | Toxicity Index (egg) |
| solid concentrate fenbutatin oxide (350 g/kg) VANISPERSE (trade mark) (100 g/kg) polyvinyl-pyrrolidone | 0.0061 | 300 | 0.0062 | 280 |
| standard suspension concentrate fenbutatin oxide (550 g/l) | 0.0195 | 100 | 0.017 | 100 |

The results set out in Tables 5 and 6 serve to confirm the results of Tables 1 and 2, and indicate further that the solid concentrate organotin formulation of the present invention exhibits significantly greater acaricidal activity than the corresponding standard commercial suspension concentrate.

EXAMPLE 12

For comparison purposes, the general method of Example 1 was used to prepare a solid concentrate formulation of polyvinylpyrrolidone and the commercially available pyrethroid insecticide alpha cypermethrin (a 1:1 reaction mixture of (S)--cyano-3-phenoxybenzyl (IR)-cis-3-(2,2-dichlorovinyl)-2,2-dimethylcyclopropane-carboxylate and (R)--cyano-3-phenoxybenzyl (IS)-cis-3-(2,2-dichlorovinyl)-2,2-dimethylcyclopropanecarboxylate). Following the general test procedure of Example 8, the acaricidal activity of the polyvinylpyrrolidone/alpha cypermethrin formulation was compared with that of a standard suspension concentrate formulation of alpha cypermethrin. The results are set out in Table 7 below:

TABLE 7

| | Time (hr) | $LC_{50}$ (%) | Toxicity Index |
|---|---|---|---|
| solid concentrate alpha cypermethrin (325 g/kg) and polyvinylpyrrolidone | 48 | >0.08 | <4 |
| | 72 | >0.08 | <4 |
| standard suspension concentrate alpha cypermethrin | 48 | >0.08 | <4 |
| | 72 | >0.08 | <4 |

The results set out in Table 7 indicate that a solid concentrate formulation of a pyrethroid insecticide, alpha cypermethrin, exhibits only an equivalent acaricidal activity to the standard suspension concentrate.

I claim:

1. A method of combating pests at a locus which comprises applying to the locus an effective amount of an aqueous dispersion comprised of a water-dispersible solid comprised of polyvinylpyrrolidone and at least one pesticidal organotin compound selected from the group consisting of a trineophyl tin and a tricycleohexyl tin compound.

2. A method according to claim 1, in which the quantity of the organotin compound present is in the range of from 10% w/w to 50% w/w.

3. A method according to claim 1, in which the quantity of polyvinylpyrrolidone present is in an amount in the range of from 50% w/w to 90% w/w.

4. A method according to claim 1, in which the polyvinyl pyrrolidone has an average molecular weight in the range of from 10,000 to 400,000.

5. A method according to claim 1, in which the organotin compound incorporated in the formulation is fenbutatin oxide.

* * * * *